United States Patent
Osa et al.

(10) Patent No.: US 8,644,903 B1
(45) Date of Patent: Feb. 4, 2014

(54) ELECTRODE FOR RECORDING AND STIMULATION

(71) Applicant: PMT Corporation, Chanhassen, MN (US)

(72) Inventors: Benjamin Osa, Chanhassen, MN (US); Eric Caille, Chanhassen, MN (US); Charles Talbott, Chanhassen, MN (US); Joseph Copley, Chanhassen, MN (US); Alfred Iversen, Chanhassen, MN (US)

(73) Assignee: PMT Corporation, Chanhassen, MN (US)

( * ) Notice: Subject to any disclaimer, the term of this patent is extended or adjusted under 35 U.S.C. 154(b) by 0 days.

(21) Appl. No.: 13/864,945

(22) Filed: Apr. 17, 2013

Related U.S. Application Data

(62) Division of application No. 12/924,657, filed on Oct. 1, 2010.

(60) Provisional application No. 61/227,928, filed on Oct. 1, 2009.

(51) Int. Cl.
- *A61B 5/0478* (2006.01)
- *A61N 1/05* (2006.01)
- *H01R 9/22* (2006.01)

(52) U.S. Cl.
USPC .......... 600/378; 600/377; 600/393; 607/116; 439/668; 439/909

(58) Field of Classification Search
USPC ........................................ 600/377, 378, 393
See application file for complete search history.

(56) References Cited

U.S. PATENT DOCUMENTS

| | | | | |
|---|---|---|---|---|
| 4,461,304 A * | 7/1984 | Kuperstein | ................... | 600/378 |
| 4,869,255 A * | 9/1989 | Putz | ............... | 600/378 |
| 5,902,236 A * | 5/1999 | Iversen | ........................ | 600/378 |
| 8,195,267 B2 * | 6/2012 | Seymour et al. | .............. | 600/377 |

* cited by examiner

*Primary Examiner* — Lee S Cohen
(74) *Attorney, Agent, or Firm* — Anthony G. Eggink; Katrina M. Eggink; Eggink & Eggink

(57) ABSTRACT

Improved electrode assemblies for recording and stimulation. Cortical and depth electrode structures are provided as well as inline interconnection systems. Methods of manufacture are further taught to provide enhanced surfaces for cortical electrodes. The inline interconnection systems include connector assembly embodiments for electrode leads which have structure providing ease of EEG recording as well as stimulation.

20 Claims, 8 Drawing Sheets

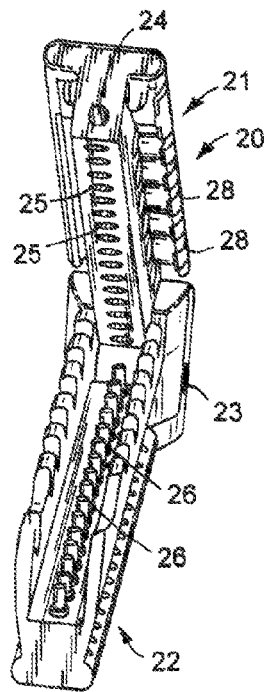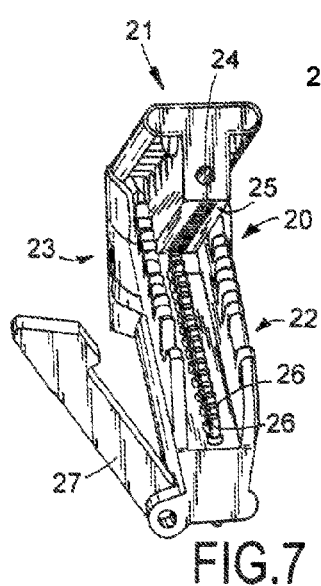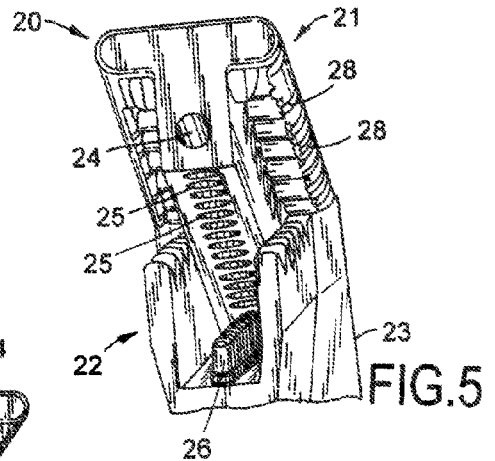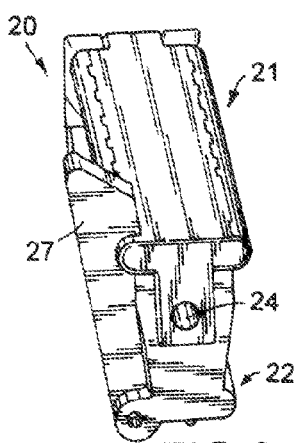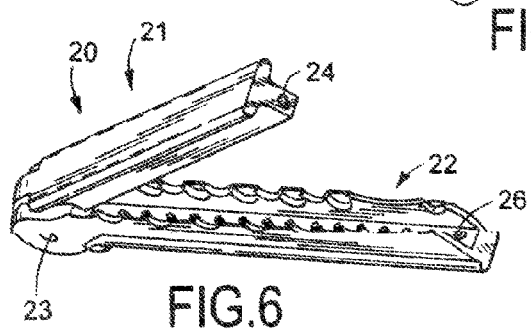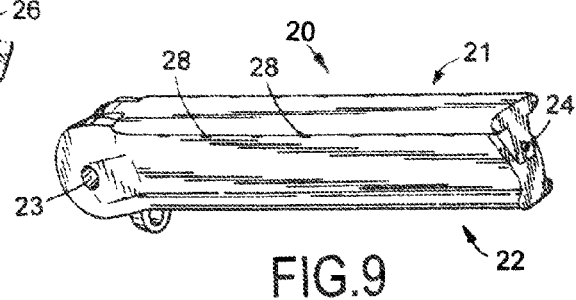

64 CONTACT GRID

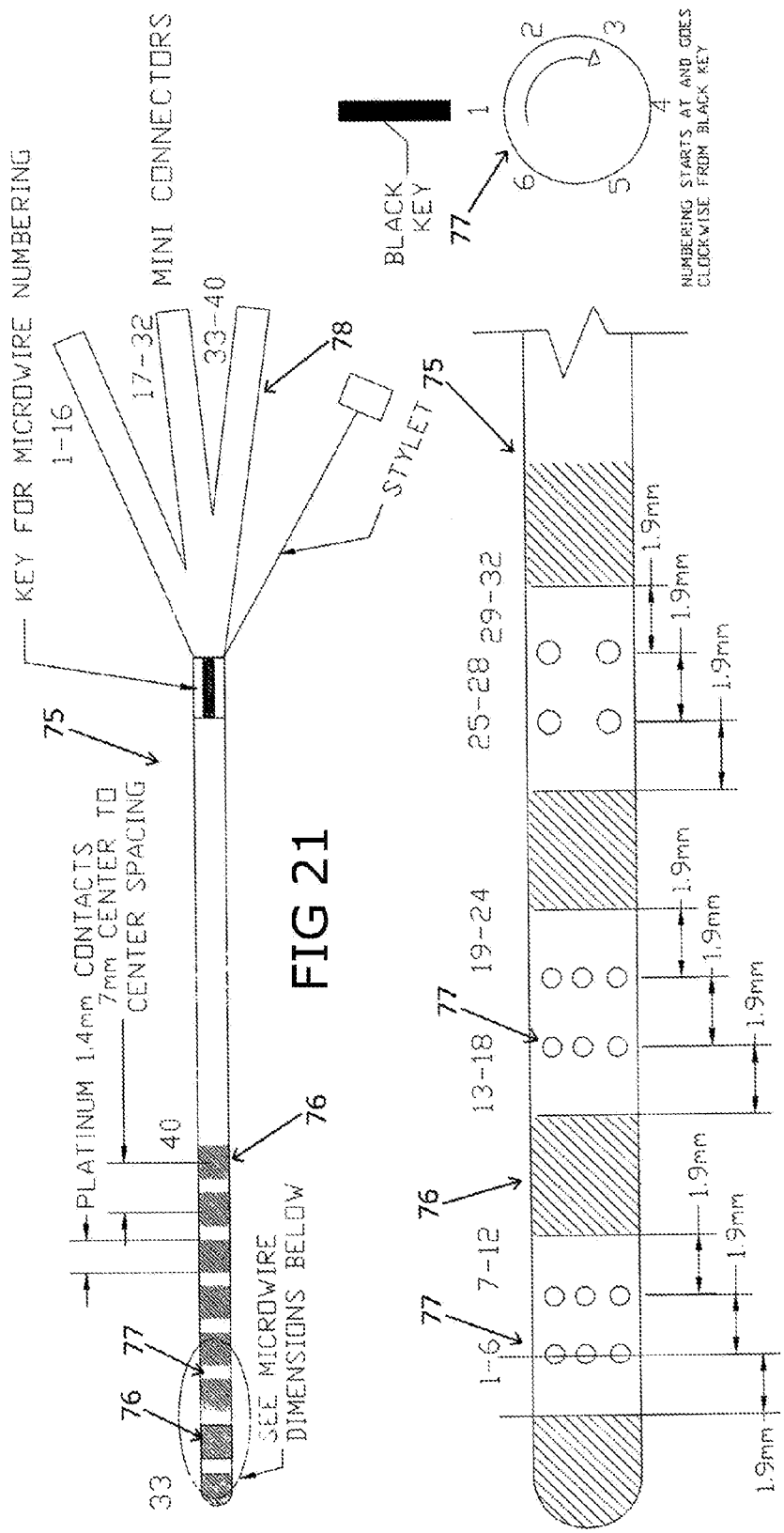

ELECTRODE FOR RECORDING AND STIMULATION

This Application is a Division of patent application Ser. No. 12/924,657, filed Oct. 1, 2010, now U.S. Pat. No. 8,435, 079, and claims the benefit of U.S. Provisional Patent Application Ser. No. 61/227,928, filed on Oct. 1, 2009.

BACKGROUND OF THE INVENTION

The present invention relates generally to improved electrode assemblies for recording and stimulation. Particularly, this invention relates to improved electrode assembly structures, their use and method of manufacture. More particularly, the invention relates to improved cortical and depth electrode assemblies and related inline interconnection systems.

Cortical and depth electrodes are used for monitoring recordable electrical brain activity or electroencephalograph (EEG) signals when less invasive methods do not provide the electrophysiology data necessary. The electrode recording is performed directly on the surgically exposed brain and is necessary when the seizure focus is too small and/or too deep within the brain to produce a recordable EEG signal.

An adaptation of the procedure for the placement of cortical or depth electrodes also prompts the need for an improved inline interconnection system. The procedural change entailed the tunneling of the electrode tail subdermally to a site secondary to the burr-hole or craniotomy opening in the skull to lengthen the path traveled by infection. This procedural change provided the need for a small diameter cylindrical tail capable of being passed through a tunneling needle.

Applicants' assignee is the owner of U.S. Pat. Nos. 5,902, 236 ('236 patent) and 6,162,101 ('101 patent), both of which are incorporated by reference into this application. The '236 patent was issued May 11, 1999 and is entitled *Tissue Electrode for Recording and Stimulation*. The '101 patent was issued Dec. 19, 2000 and is entitled *Connector Assembly for Electrodes*. The present application discloses electrode and connector structures which are improvements of these electrodes and connector assemblies disclosed and claimed in the '236 and '101 patents.

SUMMARY OF THE INVENTION

The present invention relates to improvements for electrode assemblies used for recording and stimulation. The electrode assemblies include improved electrode structures and methods of manufacture which enhance their use and effectiveness. The assemblies further include improved connector assemblies which permit the easy and reliable connection of the electrode tail to a recording and/or stimulation machine.

The inline interconnection cable provides a link between the subdural electrode and the electroencephalograph (EEG). This interconnection cable is necessary because the electrical connectors in the tail of the cortical electrode are not directly compatible with the EEG. The cable connector has female plugs for connection to the EEG.

An advantage of the present invention is to provide enhanced surface electrodes wherein the electrode grid or strip has a textured surface to increase malleability for conformance to the surface features of the brain. Another advantage is to provide an electrode grid or strip having a textured surface to reduce adhesion to smooth and wet surfaces of the brain, dermal, and/or skull.

Another advantage is to provide a method for forming an electrode with a textured surface by means of a coating applied as a subsequent operation to the dielectric silicone or flexible polymer material. Another advantage is to provide a method for forming an electrode with a textured surface by means of a "lost wax technique" wherein salt or another water soluble material is applied to the uncured dielectric material of the grid or strip. The material then being cured and the water soluble material removed via a de-ionized (DI) water application. Another advantage is to provide an electrode with a textured surface by means of a textured feature transferred during the molding process, for example, sandblasting, knurling, or a similar means for providing the texture to the surface.

Another advantage of the present invention is to provide hinged two-piece connectors having a hinge either perpendicular or parallel to the contact pins of the connector assembly. The advantage of the connector assembly is to provide an ergonomically, user intuitive means of making inline interconnections for an electrode. The novel hinged inline connector assembly of the invention may have slots or holes used to access pins which can be used to take readings or stimulation at predetermined points of contact of the electrode. The connector assembly further uses a novel shielded cable for connection to an EEG or stimulation machine.

These and other benefits and advantages of this invention will become clear from the following description by reference to the drawings.

BRIEF DESCRIPTION OF THE DRAWINGS

FIG. 4 is a perspective view of another embodiment of the connector assembly of the invention;

FIG. 5 is a perspective view of the connector assembly of FIG. 4;

FIG. 6 is a perspective view of the connector assembly of FIG. 4;

FIG. 7 is a perspective view of the connector assembly of FIG. 4;

FIG. 8 is a perspective view of the connector assembly of FIG. 4;

FIG. 9 is a perspective view of the connector assembly of FIG. 4;

FIG. 21 is a plan view showing an eight contact depth electrode having microwire wire electrodes and mini connectors;

FIG. 22 is an enlarged plan view showing the microwire electrodes of FIG. 21;

DESCRIPTION OF THE PREFERRED EMBODIMENTS

Figure 23:
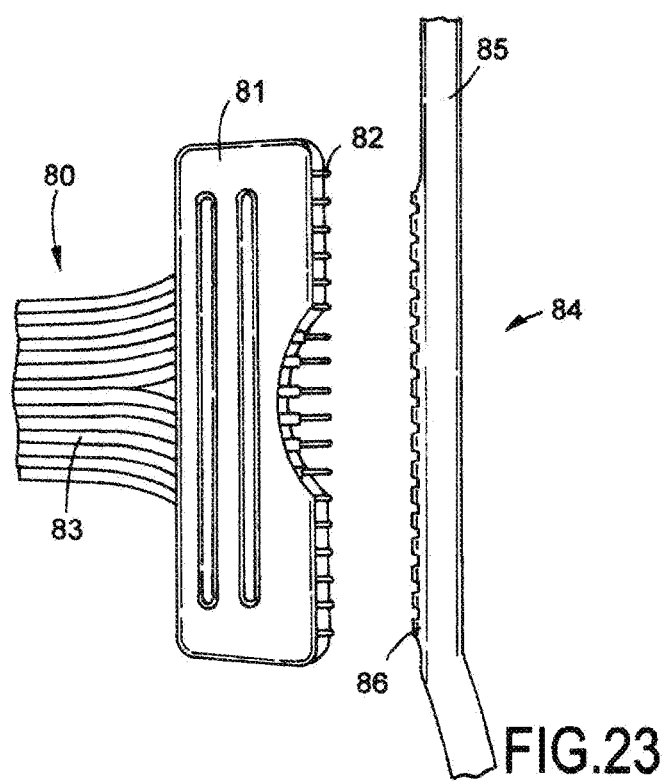
FIG. 23 is a perspective view showing an interconnection cable showing a ribbon cable with a mini connector aligned with the contacts of an electrode lead.
Figure 24:
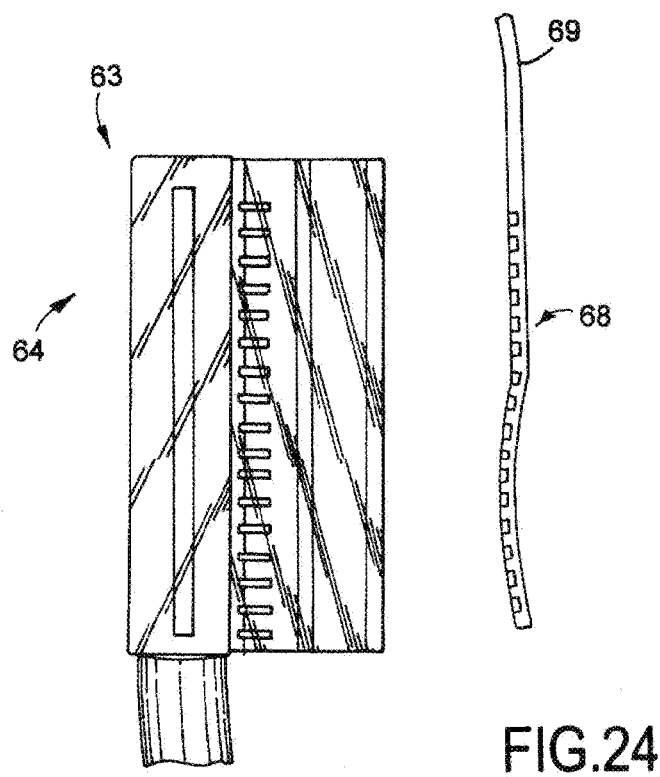
FIG. 24 is a perspective view showing an interconnection cable showing a cable with an inline connector aligned with the contacts of an electrode lead.

The present invention relates to improvements for electrode assemblies used for recording and stimulation. The improvements to the electrode assemblies are discussed below with reference to the drawings. Specifically, the connector assemblies are discussed with reference to FIGS. 1-15, and the cortical electrodes are discussed with reference to FIGS. 16-20. The electrode related drawings show cortical electrode grids and contact layouts (FIGS. 16-18, 20). Further shown in the drawings are a shielded lead (FIG. 19) used for the electrodes of the invention and depth electrode structures (FIGS. 21 and 22) and associated interconnection cables and mini connectors that provide the inline interconnection systems of the invention (FIGS. 23 and 24).

Operation of the Invention

A cortical electrode is tunneled by the electrode tail subdermally to a site secondary to the burr-hole or craniotomy opening in the skull to lengthen the path traveled by infection. A small diameter cylindrical tail is passed through a tunneling needle.

The innovative surfacing of the cortical grid and strip electrodes allows the physician to slide the electrode across the surface of the brain with less friction than a similarly disposed electrode having a non-textured surface. The textured electrode surface improves the malleability of the grid or strip, allowing it to form to the shape of the brain aiding the monitoring of the recordable electrical brain activity by providing a better connection between the brain and the contacts.

Inline Connector Assemblies

Figure 1:
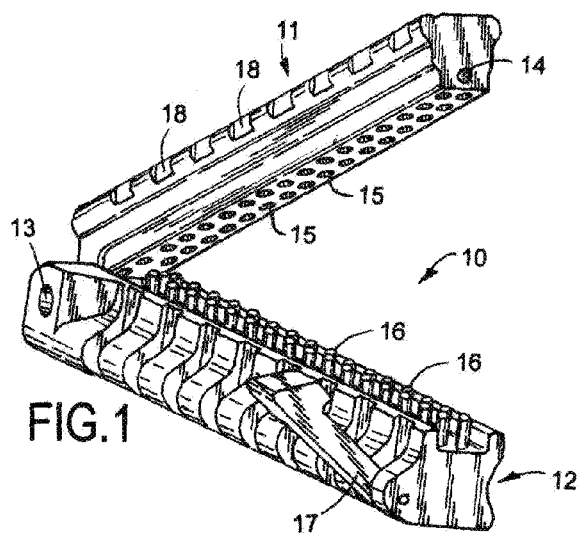
FIG. 1 is a perspective view showing an embodiment of the connector assembly of the invention.
Figure 2:
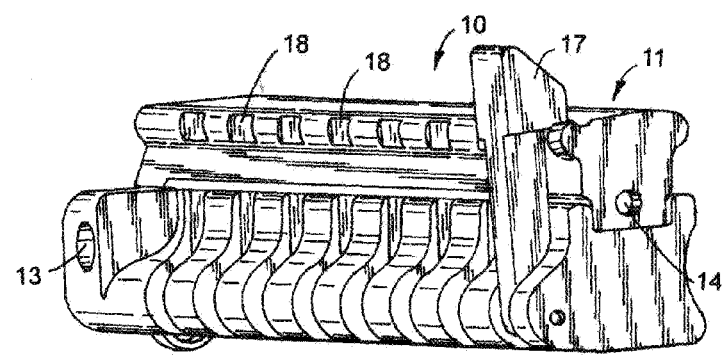
FIG. 2 is a perspective view of the connector assembly of FIG. 1.
Figure 3:
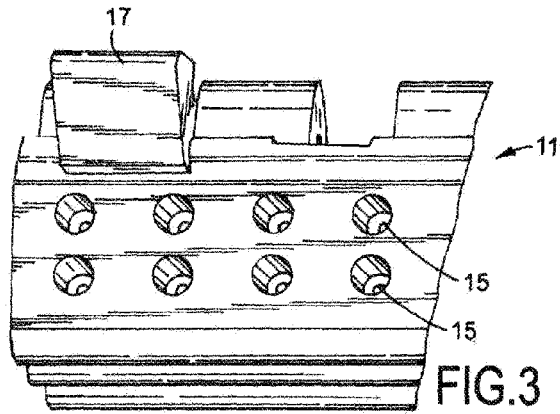
FIG. 3 is another perspective view of the connector assembly of FIG. 1.
Figure 10:
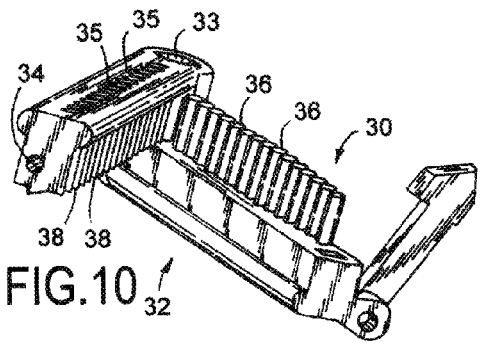
FIG. 10 is a perspective view of another embodiment of the connector assembly of the invention.
Figure 11:
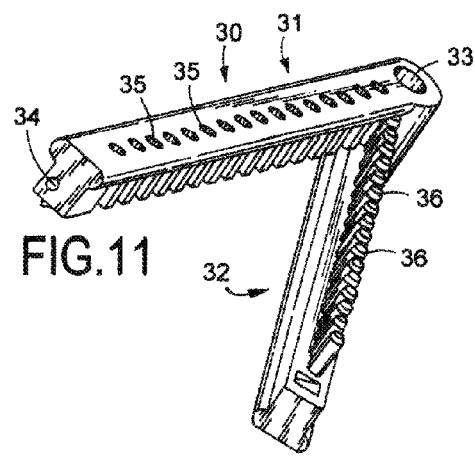
FIG. 11 is a perspective view of the connector assembly of FIG. 10.
Figure 13:
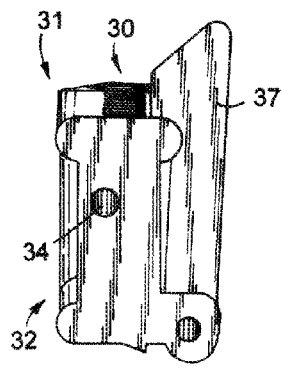
FIG. 13 is a perspective view of the connector assembly of FIG. 10.
Figure 14:
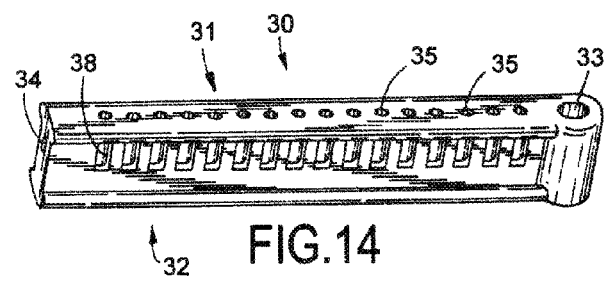
FIG. 14 is a perspective view of the connector assembly of FIG. 10.
Figure 12:
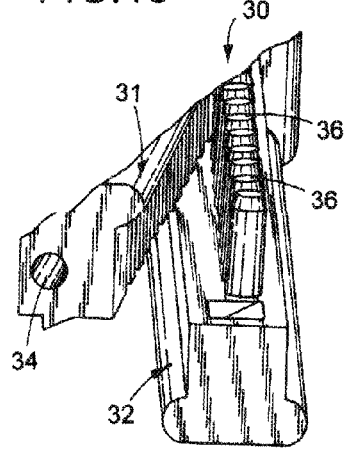
FIG. 12 is a perspective view of the connector assembly of FIG. 10.
Figure 15:
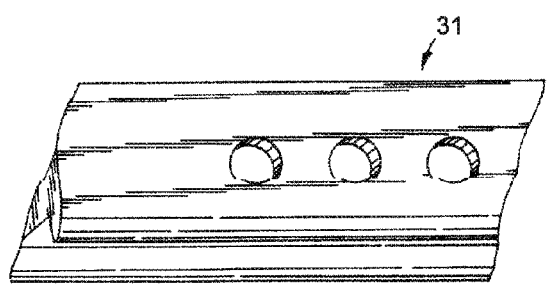
FIG. 15 is a perspective view of the connector assembly of FIG. 10.

Referring to FIGS. 1-3, the connector assembly embodiment 10 shows a hinged two-piece connector having a top member 11, and a bottom member 12. The top member rotates with respect to bottom member 12 by means of hinge 13 which is disposed perpendicular to the connector's contact pins 16 (2 rows) and positioned adjacent to the distal tip or end of the inline tail of the electrode when placed in the assembly. The contact pins 16 may be constructed of stainless steel, platinum, a platinum alloy, or of a shape memory alloy (SMA) as further discussed below.

The hinge 13 may use a dowel (not shown) that is perpendicular to the length of the inline connector structure and perpendicular to the connector pins 16 extending upwardly in the bottom body 12 of the connector assembly. The dowel may be a screw that threads into one side of the connector, a dowel with a recess for a pin, or an e-clip. The hinge 13 may also be a press fit pin that bottoms out and is sealed in or enclosed with another part, or potted into place.

The inline connector top member 11 of connector assembly 10 is shown having a single long hole or bore 14 in which the inline tail runs the length and terminates adjacent the end of top member 11. The connector bottom body 12 contains a line of two pin (16) pairs for each inline tail contact and which extend upwardly and perpendicularly along the length of the bottom body 12. The inline tail of an electrode is discussed below.

As shown, two pairs of sweeping holes 15 extend into the inline tail hole 14 of the connector top 11. The two holes 15 overlap the perimeter of the inline tail contacts and are located approximately in the mid-point of the length of each inline contact. When the inline connector top 11 swings onto the inline bottom body 12, the contacts mate inside the swept holes 15, and a compression fit is created between the two contact pins 16 and the inline tail contact. The connectors typically may have up to 16 contacts, but may have more or less.

When an inline tail is inserted into an inline connector 10, and the connector bodies 11, 12 are moved so the connector is in the "closed" position to provide a secure electrical connection and to prevent disconnection, a hinged latch 17 may be provided. The hinged latch 17 is used to prevent connectors from swinging back open. Alternatively, a spring loaded pin or ball bearing may be used to snap the two body pieces 11, 12 into a locking closed position.

Access slots, holes, or recesses 18 are provided for taking readings or performing stimulation directly at the connector 10 from the exterior of the inline top portion 11. The slots 18 extend through the body 11 so that contact with selected pins 16 may be made.

The connector assembly 10 is electrically connected by a round multi-conductor cable or a ribbon cable either with or without shielding. The end of this cable has an EEG touch-proof connector which plugs into an EEG recording machine. Another connector (quick disconnect connector) may also be positioned along this cable length, which allows for quick disconnect while the inline connector 10 is attached to the inline tail and the EEG plugs are attached to the EEG machine.

Referring to FIGS. 4-9, connector assembly embodiment 20 shows a hinged two-piece connector having a top body 21, a bottom body 22, and a hinge 23 disposed perpendicular to the connector's contact pins 26. The contact pins 26 are either spring-loaded pins or ball bearings, which may be formed of stainless steel, platinum, a platinum alloy, or the like. The hinge 23 having a dowel is shown positioned perpendicular to the length of the inline connector and perpendicular to the spring-loaded pins 26 disposed upwardly in the bottom portion 22 of the connector 20. The dowel may be a screw that threads into one side of the connector, a dowel with a recess for a pin, or an e-clip. The hinge 23 may be a press fit pin that bottoms out and is sealed in with another part or potted into place.

The inline connector top 21 of connector assembly 20 is shown having a single long hole or bore 24 in which the inline tail runs the length and terminates near the end of the top 21. The connector body bottom 22 houses one spring-loaded pin 26 for each inline tail contact and which extends perpendicularly from the length of the body 22.

One sweeping hole or bore 24 is provided for each spring-loaded pin (or ball bearing) which cuts into the inline tail hole or bore 24 on the connector top 21. These holes 25 overlap the perimeter of the inline tail contacts and are located approximately in the mid-point of the length of each inline contact. When the inline connector top 21 swings onto the inline bottom body 22, the contacts mate inside the swept holes 25, and a slight compression fit is created between the spring-loaded pin 26, the inline tail contact, and the inline tail mating hole 25 wall.

The connector assembly 20 allows for disconnection of the inline tail from a strong force to prevent potential harm to the patient. The connectors typically may have up to 16 contacts but may have more or less.

When an inline tail is inserted into an inline connector through bore 24, and the connector pieces (top 21, bottom 22) are moved so the connector is in the "closed" position to make a secure electrical connection, to prevent disconnection, a hinged latch 27 may be used. The hinged latch 27 may be used to prevent the connector assembly 20 from swinging back open. Alternatively, a spring loaded pin or ball bearing may be used to snap the two hinged pieces 21, 22 into a locking closed position.

Access slots, holes, or recesses 28 are provided for taking readings or performing stimulation directly at the top portion 21 of connector assembly 20 so that these activities may be performed from the exterior of the inline top portion 21.

The connector 20 is connected either to a round multi-conductor cable or a ribbon cable either with or without shielding. The end of this cable preferably has EEG touch-proof connectors which plug into EEG recording machines. Sometimes another connector (quick disconnect connector) is positioned along this cable length which allows for a quick disconnect, while the inline connector 20 is attached to the inline tail and the EEG plugs are attached to the EEG machine.

Referring to FIGS. 10-15, connector assembly embodiment 30 is shown having a top body 31, a bottom body 32 and a hinge 33 with a dowel which is parallel to the connector pins 36 extending upwardly form the bottom body portion 32 of the connector assembly 30. The dowel may be a screw that threads into one side of the connector, a dowel with a recess for a pin, or an e-clip. The hinge 33 may be a press fit pin with bottoms out and is sealed in with another part or potted into place. The hinge 33 is spring loaded so that the two pieces 31, 32 can create vertical space between the two pieces for swinging the two pieces into a closed position. This allows for the convex and concave triangular locking mechanism 37 on the end of the connector pieces to mate together and to lock the unit into place.

The inline connector top 31 of connector assembly 30 is shown having a single long hole or bore 34 in which the inline tail runs the length and terminates near the end of the connector top 31. The connector bottom body 32 houses pin 36 for each inline tail contact which extend perpendicularly upwards. Sweeping notches 38 in the side of the inline top cut into the inline tail hole 34 in the connector top 31. These notches 38 straddle the perimeter of the inline tail contacts and are located approximately in the midpoint of the length of each inline contact. When the inline connector top 31 swings adjacent to the inline body, the contacts 36 of the inline body mate with the swept holes and a compression fit is created between the contact pin 36, the inline tail contact, and the inline tail mating hole 34 wall. The connectors typically may have up to 16 contacts but may have more or less. The contact pins 36 may be constructed of stainless steel, platinum, a platinum alloy, or a shape memory alloy (SMA) as further discussed below.

When an inline tail is inserted into an inline connector 30, and the connector pieces 31, 32 are moved so the connector 30 is in the "closed" position to make a secure electrical connection, to prevent disconnection, the hinged latch 37 may be used. This hinged latch 37 is used to prevent connectors from swinging back open. Alternatively, a spring loaded pin or ball bearing may be used to snap the two pieces 31, 32 into a locking closed position.

Access slots, holes, or recesses 35 are provided for taking readings or performing stimulation directly at the connector from the exterior of the inline top portion 31.

The connector assembly 30 is connected to either a round multi-conductor cable or a ribbon cable either with or without shielding. The end of this cable has EEG Touch-Proof connectors which plug into EEG recording machines. Sometimes another connector (quick disconnect connector) is position along this cable length which allows for quick disconnection while the inline connector 30 is attached to the inline tail and the EEG plugs are attached to the EEG machine.

Shape Memory Alloy Inline Contacts

The inline connector embodiments 10 and 30 described above utilize compression fits to the inline tail either by compressing the tail between two pin posts or between a pin post and a tail mating hole or bore's wall. The contact pins in these embodiments are preferably constructed of a material having shape memory alloy (SMA) properties. Prior art inline contacts for cortical and depth electrodes are typically constructed of an alloy material that may either get crimped (undesirable and may lead to product failure), or may not give way under the compression pressures of the inline contacts and inline tail holes. To provide a proper compression fit, it may be desirable to have the contact shape deform when having the outside forces of compression placed on the contact. When the forces are removed from the cylindrical contact, the contact regains the pre-stressed form of a cylindrical shape. In summary, using SMA contact materials provide a more secure connection between the inline contact and the pins because the contact's surface increases the surface contact of the inline connector contact pin(s).

Cortical Electrodes

Figure 16:
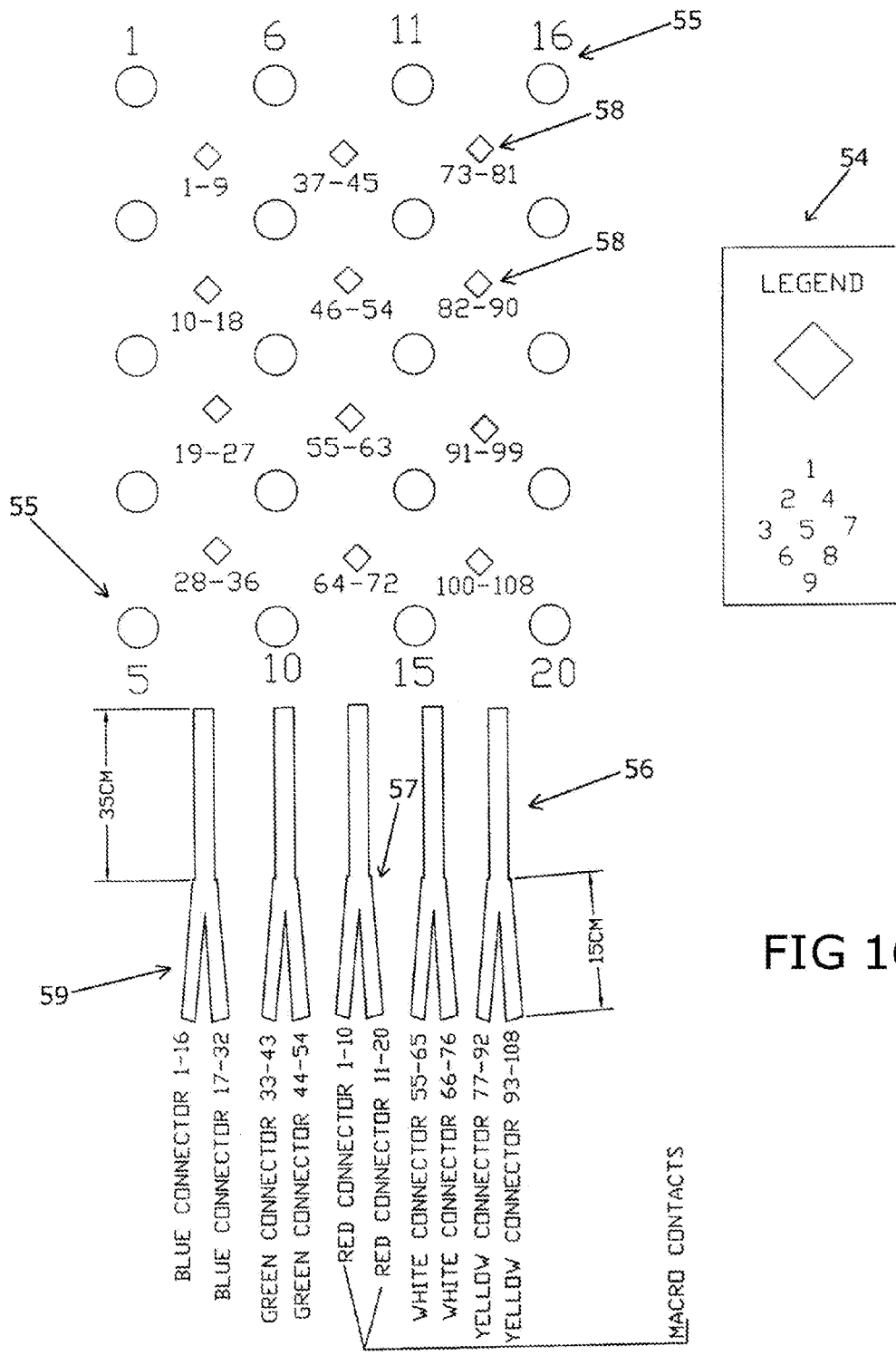
FIG. 16 is a plan view showing a cortical electrode grid of the invention.
Figure 17:
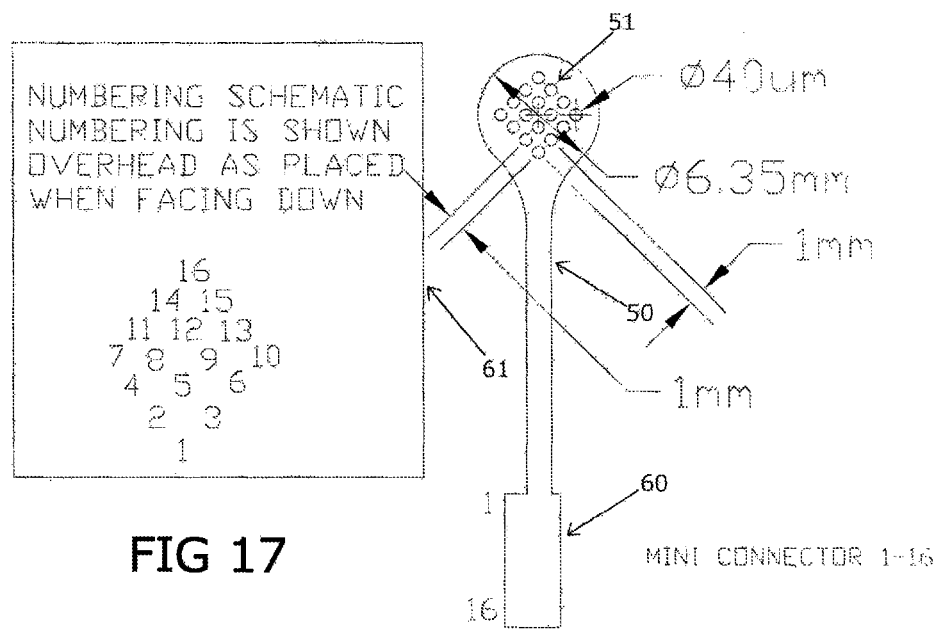
FIG. 17 is a plan view showing a contact layout of a microwire cortical electrode of the invention.
Figure 20:
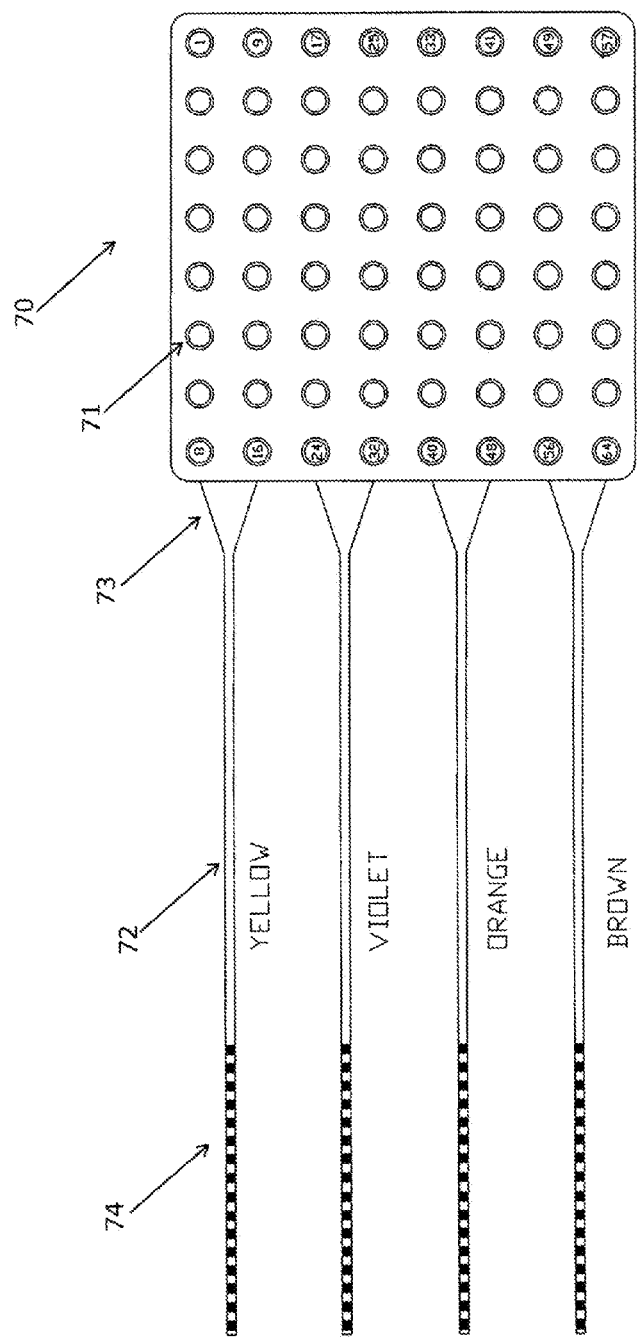
FIG. 20 is a plan view showing a contact grid, leads and tails of a cortical electrode of the invention.

Referring to FIGS. 16, 17 and 20, the cortical electrode is manufactured as a strip or a grid and consists of an elongated flexible dielectric material with front and back layers. The front layer has exposed openings for a plurality of spaced, aligned, "top-hat" designed contacts 55 (FIG. 16) sandwiched between the two layers and which protrude through the openings. The electrical contacts 55 may be fabricated from 90% platinum-10% iridium materials, or 316 stainless steel material, for example. The contacts 55 are macro contacts which are shown arranged in four rows of five contacts 55. Positioned and arranged between the macro contacts 55 are a plurality of micro contacts 58.

The lead wires 56 (FIG. 16) extend from the electrical contacts and trail to exiting tubing junctions located at either the proximal edge or from approximately the middle of the electrode. The dielectric material used in the manufacturing of the electrodes is preferably silicone or the like. Electrode strips and grids are provided in multiple shapes, sizes and thicknesses, but adequate spacing between the contacts and the edge of the electrode as well as between contacts is needed. Additionally, lead wires that exit the proximal end of the electrode may have tapered layer sections 73 (FIG. 20) to provide support to the exiting tubing. A standard strip may be approximately 10 mm wide with 3.0 mm contacts and may be approximately 0.76 mm (0.030") thick. A standard 64-contact grid (FIG. 20) may be approximately 80 mm wide, have 3.0 mm contacts and may be approximately 0.50 mm (0.020") thick.

Referring to FIG. 20, a cortical electrode 70 is shown having a contact grid 71 from which leads 72 (colored) extend and terminate at tails 74. The electrode tails 74 are shown having a plurality of spaced contacts for connection to an inline connector as discussed above. The electrode body and leads 72 are further shown to have a generally triangulated connecting portion 73 at the electrode body. Each inline connector tail of the electrode is shown to have spaced electrical contacts along the inline tail. The proximal end of each lead may be comprised of silicone tubing and securely bonded to the electrode body with liquid silicone rubber (LSR) which is subsequently cured.

The leads 56 shown in FIG. 16 are shown to extend to connectors 57. The connectors 57 and 59 provide electrical connection for both the macro and micro contacts 55, 58, respectively, and are shown to be identifiable by distinguishing colors.

A cortical grid may consist of up to four, sixteen contact inline tails. When the cortical or depth electrodes are placed using the method described above and the tails are tunneled, the exiting inline connector tail needs to be properly identified. The current state of art is the usage of colored dots or bands approximately 2 cm below the contacts on the lead array. Different colors are used for each band to properly identify each electrode tail. In the present invention, colored tubing on each individual tail is utilized to aid in identifying the corresponding location on the cortical grid. The present invention allows for better visual recognition of the corresponding electrode tails since the colored tubing extends all the way to the inline contacts. Multiple cortical strips containing 2-10 contacts in a row may also be placed and colored tubing aids to distinguish each strip (FIG. 16).

Figure 18:
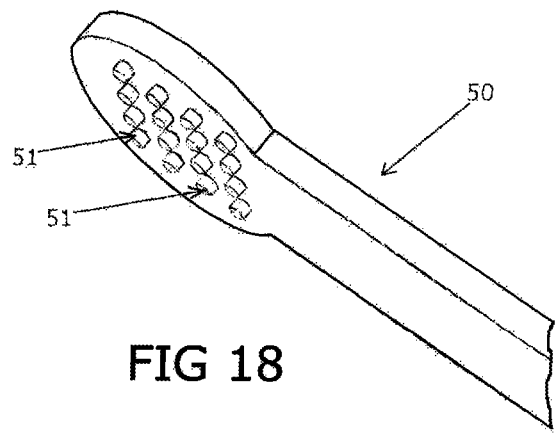
FIG. 18 is a perspective view showing a microwire cortical electrode of the invention.

Referring to FIGS. 17 and 18, a microwire cortical electrode 50 is shown having a plurality of arranged contacts 51, as shown in the numbering schematic 61. The electrode 50 is further shown having mini connector 60 for electrical contact of the electrodes (16).

Enhanced Cortical Electrode Surface

The surfaces of the cortical grid and strips are made from a flexible dielectric material such as medical grade silicone or a flexible dielectric polymer. The surfaces of the cortical grid and strips are textured to increase the flexibility of the electrode device and to prevent adherence to the smooth and/or wet surfaces of the brain or the durra.

Methods

This textured electrode surface may be created by one of three methods. The first method uses a mold or flat platens with top and bottom surfaces that are sandblasted, knurled, crosshatched with a cutting device, or other method of creating higher and lower elevations of peaks and ridges of a small dimension preferably less than 0.2 millimeters, as the final step in creating the molds. The second method uses a coating which replicates the fine textured surface created from the first method described above. Such coating process would be performed as a secondary operation after the construction of the device. The third method uses the "lost wax technique" wherein a water dissolvable material, such as salt, is molded into the surfaces of the electrode substrate that is unvulcanized or partially vulcanized. Once the unit is fully cured after the heat-press molding process or pressing and then heat curing, the unit is then washed with DI water to remove salt from the surfaces.

The textured surface on the grid or strip is only on the dielectric substrate material of silicone or the like. The texturing surfacing is not performed on any of the contacts made out of conductive materials such as stainless steel, platinum, or platinum alloy.

Temperatures in the range of 60-80 degrees Fahrenheit are suggested for the silicone to allow it to conform to the textured surfaces of the mold during the manufacturing process.

The inline cortical electrode with "top-hat" contacts provide for greater contact with the adjoining surface and the inline tails extending out from the cortical grid or strip surface. The tubing leading from the grid or strip to the connector tail is colored to aid in identifying the corresponding contacts on the electrode.

Shielded Leads Extending from Cortical or Depth Electrodes

Figure 19:
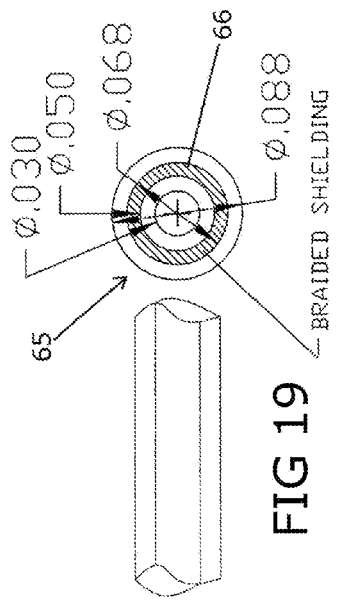
FIG. 19 is a sectional view showing a shielded lead used for the electrodes of the invention.

Referring to FIG. 19, a shielded cable 65 configuration is shown for the leads on the cortical and depth electrodes. The shielded cable structure 65 has a concentric layer of silicone or another bio-compatible material around the perimeter of the tubing. There may also be silicone or other bio-compatible material concentric inside the cross section of the shielded lead.

Shielding may be tape or braided shielding 66 made from a ferrous material. The purpose of using shielding for the leads is to prevent the leads from picking up various magnetic and radio frequency energy that may be picked up by sensitive EEG recording/monitoring equipment. Shielding the lead length, which is typically 35 cm but may be longer or shorter in length, provide readings and recordings with less image artifact, aiding medical professionals by being able to provide a better diagnosis of the patient's ailments, that being the purpose of using the electrodes.

Referring to FIGS. 21 and 22, a depth electrode 75 is shown having eight spaced contacts 76 between which two rows of micro contacts are peripherally positioned. A key 77 is shown for the microwire numbering and a number of mini connectors 78 are shown at the end of the electrode structure.

Referring to FIG. 23, a mini connector 81 is shown as part of the interconnection cable structure 80. The mini connector 81 is attached to ribbon cable 83 and has a plurality of aligned contacts 82. Sixteen contacts 82 are shown and are further shown aligned for insertion into the contacts 86 of mini connector 85 which is shown extending from the tubing lead 85 which extends to the electrode body structures (not shown).

FIG. 24 shows an interconnection cable structure 63 having an inline connector with cable structure 64 which is shown aligned for contact with an electrode lead 68 which is shown at the terminal end of tubing (silicone) 69 which is connected to an electrode.

As many changes are possible to the improved electrode assemblies for recording and stimulation and connector devices of this invention utilizing the teachings thereof, the descriptions above and the accompanying drawings should be interpreted in the illustrative and not in the limited sense.

That which is claimed is:

1. A cortical electrode comprising a strip body of elongated flexible dielectric material having front and back layers, said front layer having a plurality of openings in a predetermined arrangement, a plurality of electrode contacts extending through said openings, a lead wire extending from each said electrode contacts, said strip body having a proximal edge and having at least one tubing junction at said proximal edge of said strip body, said lead wires extending through said at least one tubing junction, said front and back layers having a textured surface to increase flexibility and to prevent adherence to smooth wet surfaces of brain tissue and dura matter.

2. The cortical electrode of claim 1, wherein said textured surface comprises peaks and ridges having a height of less than 0.2 millimeters.

3. The cortical electrode of claim 1, wherein said electrode contacts comprise top hat electrode contact structures for extending outward from said front layer of said strip body.

4. The cortical electrode of claim 1, wherein said lead wires extending from said at least one tubing junction have distinct colors for identification.

5. The cortical electrode of claim 4, wherein said lead wires are shielded.

6. The cortical electrode of claim 5, wherein said shielded lead wires include a ferrous material and a concentric layer of silicone.

7. The cortical electrode of claim 1 wherein said lead wires terminate into a tail having corresponding tail contacts.

8. A cortical electrode comprising a strip body of elongated flexible dielectric material having front and back layers, said front layer having a plurality of openings in a predetermined arrangement, a plurality of electrode contacts extending through said openings, a plurality of lead wires, wherein one lead wire extends from each said electrode contacts, said strip body having at least one tubing junction extending from the proximal edge of said strip body, said lead wires extending through said at least one tubing junction, said front and back layers having a textured surface to increase flexibility and to prevent adherence to smooth wet surfaces of brain tissue and dura matter, said textured surface having peaks and ridges.

9. The cortical electrode of claim 8, wherein said flexible dielectric material is a flexible polymeric material and wherein said peaks and ridges of said textured surface of said polymeric material have a height of less than 0.2 millimeters.

10. The cortical electrode of claim 8, wherein said electrode contacts comprise top hat contact structures.

11. The cortical electrode of claim 8, wherein said plurality of lead wires have distinct colors for identification.

12. The cortical electrode of claim 8, wherein said lead wires are shielded.

13. The cortical electrode of claim 12, wherein said shielded lead wires include a ferrous material and a concentric layer of silicone or other biocompatible material.

14. A cortical electrode comprising a strip body of elongated flexible dielectric material having front and back layers, said front layer having a plurality of openings in a predetermined arrangement, a plurality of electrode contacts aligned with and extending through said openings of said top layer, a plurality of lead wires wherein one lead wire extends from each said electrode contacts, said strip body having at least one tubing junction extending from the proximal edge of said strip body, said lead wires extending through said at least one tubing junction, said front and back layers having a textured surface to increase flexibility and to prevent adherence to smooth wet surfaces of brain tissue and dura matter, said plurality of lead wires extending through said at least one tubing junction being shielded.

15. The cortical electrode of claim 14, wherein said textured surface comprises peaks and ridges having a height of less than 0.2 millimeters.

16. The cortical electrode of claim 14, wherein said electrode contacts include macro and micro contacts.

17. The cortical electrode of claim 14, wherein said electrode contacts comprise top hat contact structures.

18. The cortical electrode of claim 14, wherein said plurality of lead wires have distinct colors for identification.

19. The cortical electrode of claim 14, wherein said shielded lead wires include a ferrous material and a concentric layer of a biocompatible material.

20. The cortical electrode of claim 19, wherein said ferrous material of said shielded lead wires are in a braided configuration.

* * * * *